United States Patent
Lin et al.

(10) Patent No.: US 9,233,942 B2
(45) Date of Patent: Jan. 12, 2016

(54) ALUMINA SUPPORT FOR SILVER CATALYST, PREPARATION AND USE THEREOF

(75) Inventors: Wei Lin, Beijing (CN); Jinbing Li, Beijing (CN); Jianshe Chen, Beijing (CN); Zhixiang Zhang, Beijing (CN); Qiang Lin, Beijing (CN); Jun Jiang, Beijing (CN); Shuyuan Cao, Beijing (CN); Qian Xue, Beijing (CN); Shujuan Wang, Beijing (CN); Zhiqiang Tang, Beijing (CN)

(73) Assignees: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

( * ) Notice: Subject to any disclaimer, the term of this patent is extended or adjusted under 35 U.S.C. 154(b) by 437 days.

(21) Appl. No.: 13/251,140

(22) Filed: Sep. 30, 2011

(65) Prior Publication Data
US 2012/0083613 A1    Apr. 5, 2012

(30) Foreign Application Priority Data
Sep. 30, 2010   (CN) .......................... 2010 1 0501992

(51) Int. Cl.
| | |
|---|---|
| B01J 23/50 | (2006.01) |
| C07D 301/03 | (2006.01) |
| B01J 21/04 | (2006.01) |
| B01J 23/02 | (2006.01) |
| B01J 23/04 | (2006.01) |
| B01J 23/66 | (2006.01) |
| B01J 23/68 | (2006.01) |
| B01J 35/10 | (2006.01) |
| B01J 37/00 | (2006.01) |
| B01J 37/14 | (2006.01) |

(52) U.S. Cl.
CPC ............... *C07D 301/03* (2013.01); *B01J 21/04* (2013.01); *B01J 23/02* (2013.01); *B01J 23/04* (2013.01); *B01J 23/50* (2013.01); *B01J 23/66* (2013.01); *B01J 23/688* (2013.01); *B01J 35/1009* (2013.01); *B01J 35/1038* (2013.01); *B01J 35/1042* (2013.01); *B01J 37/0009* (2013.01); *B01J 37/14* (2013.01)

(58) Field of Classification Search
None
See application file for complete search history.

(56) References Cited

U.S. PATENT DOCUMENTS

| | | | |
|---|---|---|---|
| 4,428,863 A | 1/1984 | Fry | |
| 4,994,588 A | 2/1991 | Kapicak et al. | |
| 5,063,195 A * | 11/1991 | Jin et al. .................... | 502/341 |
| 5,384,302 A | 1/1995 | Gerdes et al. | |
| 5,733,842 A | 3/1998 | Gerdes et al. | |
| 5,739,075 A * | 4/1998 | Matusz ..................... | 502/302 |
| 2004/0224841 A1 * | 11/2004 | Matusz et al. ............. | 502/347 |
| 2007/0093669 A1 | 4/2007 | Le-Khae et al. | |
| 2007/0173655 A1 | 7/2007 | Grey | |
| 2009/0177000 A1 | 7/2009 | Natal et al. | |

FOREIGN PATENT DOCUMENTS

| | | |
|---|---|---|
| CN | 1034678 | 8/1989 |
| CN | 1511632 A | 7/2004 |
| CN | 1634652 | 7/2005 |
| CN | 101007287 | 8/2007 |
| CN | 101007287 A | 8/2007 |
| CN | 101850243 A | 10/2010 |
| EP | 0207550 A1 | 1/1987 |

OTHER PUBLICATIONS

The Kinetics of the Thermal Decomposition of Potassium Nitrate and of the Reaction Between Potassium Nitrite and Oxygen. By Eli Freeman.*

* cited by examiner

*Primary Examiner* — Melvin C Mayes
*Assistant Examiner* — Colette Nguyen
(74) *Attorney, Agent, or Firm* — Novick, Kim & Lee, PLLC; Allen Xue

(57) ABSTRACT

The present invention relates to an alumina support for silver catalyst, a process for preparing said alumina support, a silver catalyst made from said alumina support, and a use of said silver catalyst in the production of ethylene oxide by the oxidization of ethylene. According to the present invention, the silver catalyst made from the support prepared by potassium melt technology can have a high selectivity.

4 Claims, No Drawings

US 9,233,942 B2

ALUMINA SUPPORT FOR SILVER CATALYST, PREPARATION AND USE THEREOF

CROSS REFERENCE TO RELATED APPLICATIONS

This application claims priority to Chinese Patent Application No. 201010501992.8 filed on Sep. 30, 2010; which is hereby incorporated by reference herein in its entirety.

FIELD OF THE INVENTION

The present invention relates to a support for silver catalyst, its preparation and its use. Specifically, the present invention an alumina support for silver catalyst, a process for preparing said alumina support, a silver catalyst made from said alumina support, and a use of said silver catalyst in the production of ethylene oxide by the oxidization of ethylene.

BACKGROUND OF THE INVENTION

Ethylene is oxidized under the action of the silver catalyst to mainly produce ethylene oxide, which is accompanied by the side reaction to produce carbon dioxide and water. The main technical properties of the silver catalyst include activity, selectivity and stability. The activity is reflected by the reaction temperature at which ethylene oxide is produced with a certain reaction load. The lower the reaction temperature is, the higher the catalyst activity is. The selectivity means the ratio of the mole of ethylene that converts to ethylene oxide to the total mole of ethylene that takes part in the reaction. The stability is reflected by the rate at which the activity or selectivity drops. The lower the dropping rate is, the better the catalyst stability is. The silver catalyst having high activity, high selectivity and good stability during the production of ethylene oxide by the oxidization of ethylene can improve the economical benefit remarkably. Thus, it is a main research object of the silver catalyst to make a silver catalyst having high activity, high selectivity and good stability. The property of the silver catalyst has a great relation with the property of the support used in the silver catalyst preparation and the preparation method of the support besides the composition of the catalyst and the preparation method of the catalyst.

The silver catalyst preparation method in the prior art comprises the steps of preparing porous support such as alumina and applying active components and promoters onto said porous support.

It is an important research aspect to add some components to alumina support to modify the support so as to improve the silver catalyst property. In this connection, alkaline-earth metal oxides or other salt compounds are added to the support.

U.S. Pat. No. 4,428,863 discloses a small amount of binder such as barium aluminate or barium silicate is used in the production of the alumina support having a high purity and a low surface area. It is alleged that the crushing strength and the wear resistance of the support can be improved. The prepared support has a specific surface area of less than 0.3 $m^2/g$, as well as low activity and low selectivity.

U.S. Pat. No. 5,384,302 alleges that the pre-treatment of alpha-alumina to reduce Na, K, Ca and Al ion contents in the support can improve the crushing strength and the wear resistance of the support.

U.S. Pat. No. 5,739,075 discloses a promoting-amount of rare-earth metal and a promoting-amount of another metal salt (alkaline-earth metal or Group VIII transition metal) is pre-doped on the surface of alumina support, followed by calcination, and then the treated support is used to produce the silver catalyst. The evaluation result shows that the dropping rate of the catalyst is lower than that of the catalyst without the pre-doping treatment.

Fluoride is a mineralizing agent and widely used in the production of alumina support.

CN Patent Publication No. 1034678A discloses mixing appropriate sizes and amounts of trihydrate alpha-alumina and pseudo-boehmite with carbonaceous material, fluxing agent, fluoride, binder and water, kneading into shape, drying, and calcining to produce the alpha-alumina support. The support has a specific surface area of 0.2-2 $m^2/g$. Pores with the radii of more than 30 μm comprise 25-10% of the total pores. The support is impregnated with silver compound and promoters, dried and activated to be used in the production of ethylene oxide by the oxidation of ethylene with a selectivity as high as 83-84%.

CN Patent Publication No. 101007287A discloses mixing certain sizes of trihydrate alpha-alumina and pseudo-boehmite with certain amounts of burnout carbonaceous material, fluxing agent, fluoride, and optional heavy alkaline-earth metal compound homogenously, followed by adding binder and water, kneading homogenously, extruding into shape, drying, and calcining to produce the alpha-alumina support. The support has a specific surface area of 0.2-2 $m^2/g$, a pore volume of 0.35-0.85 ml/g, water absorption of ≥30%, and a crushing strength of 30-120 N/particle. This support is impregnated with a solution of silver-amine complex, alkali metal compound and alkaline-earth metal compound, dried and activated to produce a silver catalyst useful for the production of ethylene oxide by the oxidation of ethylene.

CN Patent Publication No. 1634652A discloses a process for preparing the support without using a pore-forming agent. In that process, trihydrate alpha-alumina is directly mixed in a certain proportion with pseudo-boehmite, fluxing agent, and fluoride homogenously, added binder and water, kneaded homogenously, extruded into shape, dried, and calcined to produce the alpha-alumina support. The support has a specific surface area of 0.2-2.0 $m^2/g$, a pore volume of 0.35-0.85 ml/g, water absorption of ≥30%, and a crushing strength of 20-90 N/particle. This support is impregnated with a solution of silver-amine complex, alkali metal compound and alkaline-earth metal compound, dried and activated to produce a silver catalyst useful for the production of ethylene oxide by the oxidation of ethylene.

Albeit the above prior arts suggest adding alkaline-earth metal compound and fluoride to alumina starting material so as to modify alumina support and further to produce the catalyst with good activity and selectivity, there is still a continuous demand for the alumina support having better properties. According to the present invention, a potassium melt technology is adopted to prepare an alumina support, from which a silver catalyst with a higher selectivity can be made.

SUMMARY OF THE INVENTION

In view of the above-mentioned prior art circumstances, the present inventors have made deep researches in the field of the silver catalyst and its alumina support, and surprisingly found that an alumina support can be prepared by the potassium melt technology, and a silver catalyst with a higher selectivity can be made from this alumina support. Specifically, an appropriate amount of potassium compound is added to alumina starting material so as to form a melt with low melting point during the calcination of the support and achieve the liquid-phase calcination. Thus, the property of the alumina support is improved, and a higher selectivity can be obtained with the silver catalyst made from the alumina support.

Therefore, an object of the present invention is to provide a novel support for the silver catalyst. The silver catalyst made from the support has shown an excellent selectivity during the production of ethylene oxide by the oxidation of ethylene.

Another object of the present invention is to provide a process for preparing the above-mentioned support.

Another object of the present invention is to provide a silver catalyst prepared from the above-mentioned support.

Another object of the present invention is to provide a use of the above-mentioned silver catalyst in the production of ethylene oxide by the oxidation of ethylene.

Specifically, the present invention provides the following technical solutions.

According to the first aspect of the present invention, it provides an alpha-alumina support, which is characterized by a specific surface area of 0.2-2.0 m$^2$/g; a water absorption of not lower than 30%; a pore volume of 0.30-0.85 ml/g; and a potassium compound content, based on the weight of support and calculated as potassium element, of 0.001-2.0%.

In an embodiment according to the first aspect of the present invention, said alpha-alumina support is characterized by a specific surface area of 0.2-2.0 m$^2$/g; a water absorption of not lower than 30%; a pore volume of 0.30-0.85 ml/g; a potassium compound content, based on the weight of support and calculated as potassium element, of 0.001-2.0%; and a heavy alkaline-earth metal compound content, based on the weight of support and calculated as alkaline-earth metal, of 0.0-2.0%.

According to the second aspect of the present invention, it provides a process for preparing an alpha-alumina support, comprising the following steps:

I) preparing a mixture of
a) based on the total weight of the solids in the mixture, 5-90% by weight of trihydrate alpha-alumina;
b) based on the total weight of the solids in the mixture, 5-90% by weight of pseudo-boehmite;
c) based on the total weight of the solids in the mixture, 0.01-3.0% by weight of fluoride mineralizing agent;
d) based on the total weight of the solids in the mixture, 0.01-3.0% by weight of potassium compound;
e) based on the total weight of the solids in the mixture, 0-2.0% by weight of heavy alkaline-earth metal compound;
f) based on the total weight of components a) to e), 10-45% by weight of binder different from components c) to e); and
g) an appropriate amount of water;
wherein the total weight of the solids in the mixture means the total weight of components (a), (b), (c), (d) and (e);
the total amount of all solid components in the above mixture is 100% by weight,
when the above-mentioned mixture contains potassium fluoride, potassium fluoride is present in such an amount that potassium fluoride can be divided into two parts, one part is regarded as fluoride mineralizing agent, the other part is regarded as potassium compound, provided that both the amount of fluoride mineralizing agent and the amount of potassium compound meet the limitations to the amounts of components (c) and (d);
when the above-mentioned mixture contains heavy alkaline-earth metal fluoride, heavy alkaline-earth metal fluoride is present in such an amount that heavy alkaline-earth metal fluoride can be divided into two parts, one part is regarded as fluoride mineralizing agent, the other part is regarded as heavy alkaline-earth metal compound, provided that both the amount of fluoride mineralizing agent and the amount of heavy alkaline-earth metal compound meet the limitations to the amounts of components (c) and (e);

II) kneading the mixture obtained in the step (I) homogenously and extruding into shape to give shaped bodies;

III) drying the shaped bodies obtained in the step (II), and then calcining them to the alpha-alumina support; and IV) optionally, water-washing the support obtained in the step (III).

In an embodiment according to the second aspect of the present invention, the fluoride mentioned in the step (I) as component (c) is inorganic fluoride, preferably one or more of hydrogen fluoride, aluminum fluoride, ammonium fluoride, magnesium fluoride and cryolite, more preferably ammonium fluoride.

In another embodiment according to the second aspect of the present invention, the potassium compound mentioned in the step (I) as component (d) is inorganic acid salt, organic acid salt, hydroxide or mixture thereof of potassium, preferably one or more of potassium nitrate, potassium fluoride, potassium nitrite and potassium carbonate, more preferably potassium nitrate.

In another embodiment according to the second aspect of the present invention, the heavy alkaline-earth metal compound mentioned in the step (I) as component (e) is selected from oxide, sulfate, acetate, nitrate, carbonate and oxalate of strontium and barium, preferably barium oxide, barium sulfate, barium nitrate, barium carbonate, or a mixture thereof.

In another embodiment according to the second aspect of the present invention, the binder mentioned in the step (I) as component (f) is an acid, preferably an aqueous nitric acid solution, wherein the volume ratio of nitric acid to water is 1:1.25-1:10, preferably 1:2-1:4.

In another embodiment according to the second aspect of the present invention, in the step (I), based on the total weight of the solids in the mixture prepared in the step (I), the amount of component (a) is 15-85% by weight, the amount of component (b) is 10-80% by weight, the amount of component (c) is 0.1-2.5% by weight, the amount of component (d) is 0.1-2.5% by weight, the amount of component (e) is 0-1.0% by weight, and, based on the total weight of components (a) to (e), the amount of component (f) is 10-35% by weight;

preferably, based on the total weight of the solids in the mixture prepared in the step (I), the amount of component (a) is 35-82% by weight, the amount of component (b) is 15-62% by weight, the amount of component (c) is 1.2-2.0% by weight, the amount of component (d) is 0.3-1.2% by weight, the amount of component (e) is 0-0.5% by weight, and, based on the total weight of components (a) to (e), the amount of component (f) is 10-25% by weight;

more preferably, based on the total weight of the solids in the mixture prepared in the step (I), the amount of component (a) is 65-82% by weight, the amount of component (b) is 15-32% by weight, the amount of component (c) is 1.2-2.0% by weight, the amount of component (d) is 0.4-1.0% by weight, the amount of component (e) is 0-0.5% by weight, and, based on the total weight of components (a) to (e), the amount of component (f) is 10-25% by weight;

further more preferably, based on the total weight of the solids in the mixture prepared in the step (I), the amount of component (a) is 66.5-82% by weight, the amount of component (b) is 15-30% by weight, the amount of component (c) is 1.2-2.0% by weight, the amount of component (d) is 0.4-1.0% by weight, the amount of component (e) is 0-0.5% by weight, and, based on the total weight of components (a) to (e), the amount of component (f) is 10-25% by weight;

still further more preferably, based on the total weight of the solids in the mixture prepared in the step (I), the amount of component (a) is 66.5-82% by weight, the amount of component (b) is 15-30% by weight, the amount of component (c) is 1.2-2.0% by weight, the amount of component (d) is 0.4-1.0% by weight, the amount of component (e) is 0.2-0.5% by weight, and, based on the total weight of components (a) to (e), the amount of component (f) is 10-25% by weight;

wherein the total weight of the solids in the mixture means the total weight of components (a), (b), (c), (d) and (e);

wherein the total amount of all solid components in the mixture prepared in the step (I) is 100% by weight, when the above-mentioned mixture contains potassium fluoride, potassium fluoride is present in such an amount that potassium fluoride can be divided into two parts, one part is regarded as fluoride mineralizing agent, the other part is regarded as potassium compound, provided that both the amount of fluoride mineralizing agent and the amount of potassium compound meet the limitations to the amounts of components (c) and (d); when the above-mentioned mixture contains heavy alkaline-earth metal fluoride, heavy alkaline-earth metal fluoride is present in such an amount that heavy alkaline-earth metal fluoride can be divided into two parts, one part is regarded as fluoride mineralizing agent, the other part is regarded as heavy alkaline-earth metal compound, provided that both the amount of fluoride mineralizing agent and the amount of heavy alkaline-earth metal compound meet the limitations to the amounts of components (c) and (e).

According to the third aspect of the present invention, the present invention provides a silver catalyst useful for producing ethylene oxide by the oxidation of ethylene, wherein said catalyst comprises the alpha-alumina support prepared according to the second aspect of the present invention or the alpha-alumina support according to the first aspect of the present invention, and silver deposited thereon, an optional alkali metal promoter, an optional alkaline-earth metal promoter, and an optional rhenium promoter and optionally its co-promoter, wherein calculated on silver atom, silver is present in the silver catalyst in an amount of 1-40%, preferably 5-25%, based on the total weight of the silver catalyst, wherein calculated on alkali metal atom, the optional alkali metal promoter is present in the silver catalyst in an amount of 0-2000 ppm, preferably 5-2000 ppm, more preferably 5-1500 ppm, based on the total weight of the silver catalyst, wherein calculated on rhenium atom, the optional rhenium promoter is present in the silver catalyst in an amount of 0-2000 ppm, preferably 10-2000 ppm, more preferably 100-1000 ppm, based on the total weight of the silver catalyst, wherein calculated on alkaline-earth metal atom, the optional alkaline-earth metal promoter is present in the silver catalyst in an amount of 0-10000 ppm, preferably 0-8000 ppm, based on the total weight of the silver catalyst.

In an embodiment according to the third aspect of the present invention, said silver catalyst is prepared by the method comprising the following steps:

1) Impregnating the alpha-alumina support prepared according to the second aspect of the present invention or impregnating the alpha-alumina support according to the first aspect of the present invention with a solution containing sufficient amounts of a silver compound, an organic amine, an optional alkali metal promoter, an optional alkaline-earth metal promoter, and an optional rhenium promoter and optionally its co-promoter;

2) Filtering the impregnation solution; and

3) Activating the support obtained in the step (2) in an oxygen-containing gas to produce the silver catalyst.

In another embodiment according to the third aspect of the present invention, the silver compound is silver oxide, silver nitrate and/or silver oxalate, and the silver compound is used in such an amount that calculated on silver atom, silver is present in the silver catalyst in an amount of 1-40%, preferably 5-25%, based on the total weight of the silver catalyst;

the alkali metal promoter is one or more of lithium, sodium, potassium, rubidium and cesium compounds, preferably cesium nitrate, lithium nitrate and/or potassium hydroxide, more preferably cesium nitrate, and the alkali metal promoter is used in such an amount that calculated on alkali metal atom, the alkali metal promoter is present in the silver catalyst in an amount of 0-2000 ppm, preferably 5-2000 ppm, more preferably 5-1500 ppm, based on the total weight of the silver catalyst;

the rhenium promoter is one or more of rhenium oxide, perrhenic acid, cesium perrhenate and ammonium perrhenate, preferably ammonium perrhenate, and the rhenium promoter is used in such an amount that calculated on rhenium atom, the rhenium promoter is present in the silver catalyst in an amount of 0-2000 ppm, preferably 10-2000 ppm, more preferably 100-1000 ppm, based on the total weight of the silver catalyst; and the alkaline-earth metal promoter is one or more of magnesium, calcium, strontium and barium compounds, preferably barium compound and/or strontium compound, such as one or more of oxide, oxalate, sulfate, acetate and nitrate of magnesium, calcium, strontium and barium, and the alkaline-earth metal promoter is used in such an amount that calculated on alkaline-earth metal atom, the alkaline-earth metal promoter is present in the silver catalyst in an amount of 0-10000 ppm, preferably 0-8000 ppm, based on the total weight of the silver catalyst.

In another embodiment according to the third aspect of the present invention, the activating in the step (3) is conducted in air or a nitrogen-oxygen mixed gas with oxygen content of 21 vol % or less.

In another embodiment according to the third aspect of the present invention, in the step (3), the activating is conducted at a temperature of 180-700° C., preferably 200-500° C. for 1-120 mins, preferably 2-60 mins.

According to the fourth aspect of the present invention, the present invention provides a use of the silver catalyst according to the third aspect of the present invention to produce ethylene oxide by the oxidation of ethylene.

These aspects and other objects, features and advantages of the present invention will be more apparent upon reading the specification.

DETAILED DESCRIPTION OF THE INVENTION

According to one aspect of the present invention, the present invention provides a process for preparing alpha-alumina support for silver catalyst useful for producing ethylene oxide by the oxidation of ethylene, wherein said process comprises the following steps:

I) preparing a mixture of a) based on the total weight of the solids in the mixture, 5-90% by weight of trihydrate alpha-alumina;

b) based on the total weight of the solids in the mixture, 5-50% by weight of pseudo-boehmite;

c) based on the total weight of the solids in the mixture, 0.01-3.0% by weight of fluoride mineralizing agent;

d) based on the total weight of the solids in the mixture, 0.01-3.0% by weight of potassium compound;

e) based on the total weight of the solids in the mixture, 0-2.0% by weight of heavy alkaline-earth metal compound;

f) based on the total weight of components a) to e), 10-45% by weight of binder different from components c) to e); and g) an appropriate amount of water;

the total amount of all solid components in the above mixture is 100% by weight, when the above-mentioned mixture contains potassium fluoride, potassium fluoride is present in such an amount that potassium fluoride can be divided into two parts, one part is regarded as fluoride mineralizing agent, the other part is regarded as potassium compound, provided that both the amount of fluoride mineralizing agent and the amount of potassium compound meet the limitations to the amounts of components (c) and (d);

when the above-mentioned mixture contains heavy alkaline-earth metal fluoride, heavy alkaline-earth metal fluoride is present in such an amount that heavy alkaline-earth metal fluoride can be divided into two parts, one part is regarded as fluoride mineralizing agent, the other part is regarded as heavy alkaline-earth metal compound, provided that both the amount of fluoride mineralizing agent and the amount of heavy alkaline-earth metal compound meet the limitations to the amounts of components (c) and (e);

II) kneading the mixture obtained in the step (I) homogenously and extruding into shape to give shaped bodies;

III) drying the shaped bodies obtained in the step (II), and then calcining them to the alpha-alumina support; and IV) optionally, water-washing the support obtained in the step (III).

According to one aspect of the present invention, the present invention provides a process for preparing alpha-alumina support for silver catalyst useful for producing ethylene oxide by the oxidation of ethylene, wherein said process comprises the following steps:

I) preparing a mixture of a) based on the total weight of the solids in the mixture, 5-90% by weight of trihydrate alpha-alumina;

b) based on the total weight of the solids in the mixture, 5-90% by weight of pseudo-boehmite;

c) based on the total weight of the solids in the mixture, 0.01-3.0% by weight of fluoride mineralizing agent;

d) based on the total weight of the solids in the mixture, 0.01-3.0% by weight of potassium compound;

e) based on the total weight of the solids in the mixture, 0-2.0% by weight of heavy alkaline-earth metal compound;

f) based on the total weight of components a) to e), 10-45% by weight of binder different from components c) to e); and g) an appropriate amount of water;

the total amount of all solid components in the above mixture is 100% by weight, when the above-mentioned mixture contains potassium fluoride, potassium fluoride is present in such an amount that potassium fluoride can be divided into two parts, one part is regarded as fluoride mineralizing agent, the other part is regarded as potassium compound, provided that both the amount of fluoride mineralizing agent and the amount of potassium compound meet the limitations to the amounts of components (c) and (d);

when the above-mentioned mixture contains heavy alkaline-earth metal fluoride, heavy alkaline-earth metal fluoride is present in such an amount that heavy alkaline-earth metal fluoride can be divided into two parts, one part is regarded as fluoride mineralizing agent, the other part is regarded as heavy alkaline-earth metal compound, provided that both the amount of fluoride mineralizing agent and the amount of heavy alkaline-earth metal compound meet the limitations to the amounts of components (c) and (e);

II) kneading the mixture obtained in the step (I) homogenously and extruding into shape to give shaped bodies;

III) drying the shaped bodies obtained in the step (II), and then calcining them to the alpha-alumina support; and IV) optionally, water-washing the support obtained in the step (III).

According to the present invention, the total weight of the solids in the mixture means the total weight of components (a), (b), (c), (d) and (e).

In order to prepare the alpha-alumina support of the present invention, it is necessary to use trihydrate alpha-alumina, i.e., component (a). Based on the total weight of the solids in the mixture, i.e., based on the total weight of the solids in the mixture prepared in the step (I), trihydrate alpha-alumina is usually used in an amount of 5-90% by weight, preferably 15-80% by weight, more preferably 35-80% by weight, particularly preferably 65-80% by weight.

In one embodiment, the used amount of component (a) is 5-90% by weight, or 15-85% by weight, or 35-82% by weight, or 65-82% by weight, or 66.5-82% by weight, or 66.5-82% by weight, based on the total weight of the solids in the mixture.

Based on the total weight of the solids in the mixture, i.e., based on the total weight of the solids in the mixture prepared in the step (I), pseudo-boehmite, as component (b), is usually used in an amount of 5-50% by weight, preferably 10-40% by weight, more preferably 15-40% by weight, particularly preferably 15-30% by weight.

In one embodiment, the used amount of component (b) is 5-90% by weight, or 10-80% by weight, or 15-62% by weight, or 15-32% by weight, or 15-30% by weight, based on the total weight of the solids in the mixture.

During the preparation of the alpha-alumina support of the present invention, the fluoride is added as component (c) so as to accelerate the alumina crystal form conversion and therefore used as mineralizing agent. The fluoride used in the present invention is an inorganic fluoride, comprising hydrogen fluoride, ammonium fluoride, aluminum fluoride, magnesium fluoride, cryolite and the like, preferably one or more of hydrogen fluoride, aluminum fluoride, ammonium fluoride, magnesium fluoride and cryolite, more preferably ammonium fluoride. For the purpose of the present invention, based on the total weight of the solids in the mixture, i.e., based on the total weight of the solids in the mixture prepared in the step (I), the fluoride is usually added in an amount of 0.01-3.0% by weight, preferably 0.1-2.5% by weight, particularly preferably 1.2-2.0% by weight.

The potassium compound is added as component (d) so as to form a melt with low melting point during the calcination of the support and achieve the liquid-phase calcination. Thus, the property of the alumina support is improved, and a higher selectivity can be obtained with the silver catalyst made from the alumina support. The potassium compound used in the present invention is potassium-containing inorganic or organic compound, including inorganic acid salt, organic acid salt and hydroxide of potassium and the like, for example, potassium nitrate, potassium nitrite, potassium carbonate, potassium bicarbonate, potassium fluoride, potassium sulfate, potassium stearate, potassium silicate, potassium oxalate, potassium acetate, potassium hydroxide, potassium meta-aluminate and the like, preferably one or more of potassium nitrate, potassium fluoride, potassium carbonate and potassium nitrite, more preferably potassium nitrate. For the purpose of the present invention, based on the total weight of the solids in the mixture, i.e., based on the total weight of the solids in the mixture prepared in the step (I), the potassium compound is usually added in an amount of 0.01-3.0% by weight, preferably 0.1-2.5% by weight, more preferably 0.3-1.2% by weight, particularly preferably 0.4-1.0% by weight. When the above-mentioned mixture contains potassium fluoride, potassium fluoride is present in such an amount that potassium fluoride can be divided into two parts, one part is regarded as fluoride mineralizing agent, the other part is regarded as potassium compound, provided that both the amount of fluoride mineralizing agent and the amount of potassium compound meet the limitations to the amounts of components (c) and (d).

During the preparation of the alpha-alumina support of the present invention, the heavy alkaline-earth metal compound, i.e., component (e), can be optionally used in the step (I) for the purpose of modifying the property of the support. The heavy alkaline-earth metal compound is selected from compounds of the elements of the group IIA of the periodic table, for example, strontium and/or barium compound, e.g. oxide, sulfate, acetate, nitrate, carbonate and oxalate of strontium and/or barium. It is particularly preferable to use barium oxide, barium sulfate, barium nitrate, barium carbonate, or a mixture thereof as the heavy alkaline-earth metal compound. Based on the total weight of the solids in the mixture, i.e., based on the total weight of the solids in the mixture prepared in the step (I), the heavy alkaline-earth metal compound, particularly strontium and/or barium compound is added in an amount of 0-2.0%, preferably 0-1.0% by weight, particularly preferably 0-0.5% by weight. When the above-mentioned mixture contains heavy alkaline-earth metal fluoride, heavy alkaline-earth metal fluoride is present in such an amount that heavy alkaline-earth metal fluoride can be divided into two parts, one part is regarded as fluoride mineralizing agent, the other part is regarded as heavy alkaline-earth metal compound, provided that both the amount of fluoride mineralizing agent and the amount of heavy alkaline-earth metal compound meet the limitations to the amounts of components (c) and (e).

In one embodiment, the used amount of component (e) is 0-2.0% by weight, or 0-1.0% by weight, or 0-0.5% by weight, or 0.2-0.5% by weight, based on the total weight of the solids in the mixture. When the above-mentioned mixture contains heavy alkaline-earth metal fluoride, heavy alkaline-earth metal fluoride is present in such an amount that heavy alkaline-earth metal fluoride can be divided into two parts, one part is regarded as fluoride mineralizing agent, the other part is regarded as heavy alkaline-earth metal compound, provided that both the amount of fluoride mineralizing agent and the amount of heavy alkaline-earth metal compound meet the limitations to the amounts of components (c) and (e).

During the preparation of the alpha-alumina support of the present invention, a binder can be added as component (f). The binder and pseudo-boehmite in the mixture form an alumina sol, which bind components in the mixture together to form an extrudable paste. The binder comprises an acid, such as nitric acid, formic acid, acetic acid, propionic acid, hydrochloric acid and the like. Alternatively, the acid and pseudo-boehmite can be replaced by alumina sol. In case of using the acid as binder, it is preferable to use an aqueous nitric acid solution, wherein the volume ratio of nitric acid to water is 1:1.25-1:10, preferably 1:2-1:4. For the purpose of the present invention, the binder is usually added in an amount of, based on the total weight of components (a) to (e), 10-45% by weight, preferably 10-35% by weight, particularly preferably 10-25% by weight.

In one preferable embodiment for preparing the alpha-alumina support of the present invention, in the step (I), based on the total weight of the solids in the mixture, i.e., based on the total weight of the solids in the mixture prepared in the step (I), the amount of component (a) is 15-80% by weight, preferably 35-80% by weight, the amount of component (b) is 10-40% by weight, preferably 15-40% by weight, the amount of component (c) is 0.1-2.5% by weight, preferably 1.2-2.0% by weight, the amount of component (d) is 0.1-2.5% by weight, preferably 0.3-1.2% by weight, the amount of component (e) is 0-1.0% by weight, preferably 0-0.5% by weight, and based on the total weight of components (a) to (e), the amount of component (f) is 10-35% by weight, preferably 10-25% by weight, wherein the total amount of all solid components in the mixture prepared in the step (I) is 100% by weight, when the above-mentioned mixture contains potassium fluoride, potassium fluoride is present in such an amount that potassium fluoride can be divided into two parts, one part is regarded as fluoride mineralizing agent, the other part is regarded as potassium compound, provided that both the amount of fluoride mineralizing agent and the amount of potassium compound meet the limitations to the amounts of components (c) and (d); when the above-mentioned mixture contains heavy alkaline-earth metal fluoride, heavy alkaline-earth metal fluoride is present in such an amount that heavy alkaline-earth metal fluoride can be divided into two parts, one part is regarded as fluoride mineralizing agent, the other part is regarded as heavy alkaline-earth metal compound, provided that both the amount of fluoride mineralizing agent and the amount of heavy alkaline-earth metal compound meet the limitations to the amounts of components (c) and (e).

In one particularly preferable embodiment for preparing the alpha-alumina support of the present invention, in the step (I), based on the total weight of the solids in the mixture, i.e., based on the total weight of the solids in the mixture prepared in the step (I), the amount of component (a) is 65-80% by weight, the amount of component (b) is 15-30% by weight, the amount of component (c) is 1.2-2.0% by weight, the amount of component (d) is 0.4-1.0% by weight, the amount of component (e) is 0-0.5% by weight, and based on the total weight of components (a) to (e), the amount of component (f) is 10-25% by weight, wherein the total amount of all solid components in the mixture prepared in the step (I) is 100% by weight, when the above-mentioned mixture contains potassium fluoride, potassium fluoride is present in such an amount that potassium fluoride can be divided into two parts, one part is regarded as fluoride mineralizing agent, the other part is regarded as potassium compound, provided that both the amount of fluoride mineralizing agent and the amount of potassium compound meet the limitations to the amounts of components (c) and (d); when the above-mentioned mixture contains heavy alkaline-earth metal fluoride, heavy alkaline-earth metal fluoride is present in such an amount that heavy alkaline-earth metal fluoride can be divided into two parts, one part is regarded as fluoride mineralizing agent, the other part is regarded as heavy alkaline-earth metal compound, provided that both the amount of fluoride mineralizing agent and the amount of heavy alkaline-earth metal compound meet the limitations to the amounts of components (c) and (e).

After kneading the mixture in the step (I), in general, a paste is obtained. It is usually advantageous for the present invention to firstly mix components (a), (b) and (e) homogenously and charge into the kneader, and then add components (c), (d), (f) and (g) to knead into an extrudable paste. The obtained paste is extruded into shape to produce shaped bodies. The shaped bodies can be dried to a moisture content of 10 wt % or less. The drying temperature can be 80-120° C. The drying time can be controlled depending on the moisture content, for example, the drying time is 1-24 hours. The obtained shaped bodies can be in a form of ring, sphere, column or multihole column or the like.

After drying, the shaped bodies are generally calcined at a temperature of 900-1600° C., preferably 1100-1400° C. for not less than 1 hour, preferably 3-8 hours. Substantially all of alumina, for example, more than 90% of alumina can be converted to alpha-alumina by the calcination so as to obtain the alpha-alumina support.

In one preferable embodiment for preparing the alpha-alumina support of the present invention, after the step (III), the support obtained in the step (III) is water-washed. The water-washing can be conducted with distilled water or deionized water or other water, preferably deionized water. The water-washing can be done with ultrasonic technique. After water-washing, the support is dried. For example, in one preferable embodiment for water-washing, the support is placed in a vessel containing deionized water, sonically oscillated for a period of time (e.g. 5-60 mins), thereafter stood for a period of time (e.g. 5-30 mins), then filtered to remove the aqueous solution, and finally dried in a heated air stream (e.g. the air stream heated to 100-800° C.) to produce the support.

According to another aspect of the present invention, the alpha-alumina support prepared by the above-mentioned process is provided, wherein said support has a specific surface area of 0.2-2.0 $m^2/g$; a water absorption of not lower than 30%; a pore volume of 0.30-0.85 ml/g; a potassium compound content, based on the weight of support and calculated as potassium element, of 0.001-2.0%.

According to the present invention, the specific surface area of the support is measured according to the International Standard ISO-9277 by the Nitrogen Gas Physical Adsorption BET Method. For example, the specific surface area of the support can be measured with Nitrogen Gas Physical Adsorption Instrument NOVA2000e (Quantachrome Corp., USA).

According to the present invention, the pore volume of the support is measured by the mercury porosimetry. For example, the pore volume of the support can be measured with AutoPore9510-type Mercury Porosimeter (Micromeritics Instrument Corp., USA).

The radial crush strength of the support, for example, can be measured with the DL II type Particle Strength Tester (manufactured by Dalian Research and Design Institute of Chemical Industry) by randomly selecting thirty support sample particles, measuring the radial crush strength for each particle, and then calculating the average of the radial crush strength.

The content of the potassium compound in the support can be obtained by calculation or measurement (for example, X-Ray fluorescence).

The content of the alkaline-earth metal in the support can be obtained by calculation or measurement (for example, X-Ray fluorescence). The alpha-alumina support produced by the process for preparing the alumina support according to the present invention can be in a conventional form in the art, such as ring, sphere, column, multihole column or the like.

After obtaining the alpha-alumina support of the present invention, a silver catalyst can be produced in a manner known by the skilled person in the art or in a conventional manner. For example, the silver catalyst of the present invention can be produced by impregnating the above alumina support with a solution containing a silver compound and an organic amine.

The addition of the active component silver can be accomplished by a conventional impregnation method. For example, the support is impregnated in a silver-amine complex solution, and then heat-treated after removing a redundant solution by filtration. The used silver compound can be a silver precursor, such as silver oxide, silver nitrate, and silver oxalate, preferably silver oxalate. For ensuring the uniform and adequate loading of silver, the support is preferably vacuumed in advance, and immediately activated in a flowing air or inert gas such as nitrogen and argon at a temperature of 200-500° C. for 2 mins or more after the impregnation and the filtration. For ensuring that the catalyst has a relative high activity, the heat-treatment should be conducted at a temperature not higher than 500° C. For further improving the catalyst performance, an alkali metal promoter such as lithium compound, sodium compound, potassium compound, rubidium compound, cesium compound or a mixture thereof, an alkaline-earth metal promoter such as calcium compound, strontium compound, barium compound or a mixture thereof, a rhenium promoter and optionally a rhenium co-promoter, and the like, can be added to the silver catalyst of the present invention. These promoters can be applied to the support before, during or after the silver impregnation, or impregnated onto the support after the silver compound has been reduced.

In one embodiment of the present invention, the process for preparing the silver catalyst of the present invention comprises the following steps:

1) Impregnating the above alumina support with a solution containing sufficient amounts of a silver compound, an organic amine, an optional alkali metal promoter, an optional alkaline-earth metal promoter, and an optional rhenium promoter and optionally its co-promoter;

2) Filtering the impregnation solution; and

3) Activating the support obtained in the step (2) in an oxygen-containing gas to produce the silver catalyst.

The above silver compound can be any silver compound suitable for preparing the silver catalyst useful for the production of ethylene oxide. According to the present invention, it is preferable to use silver oxide, silver nitrate and/or silver oxalate. The amount of the silver compound used in the impregnation procedure should be sufficient so that the finally produced silver catalyst contains 1-40 wt %, preferably 5-25 wt % of silver calculated on the silver atom based on the total weight of the catalyst.

The above organic amine compound can be any organic amine compound suitable for preparing the silver catalyst useful for the production of ethylene oxide, provided that the organic amine compound has an ability to form a silver-amine complex with the silver compound. According to the present invention, it is preferable to use pyridine, butyl amine, ethylene diamine, 1,3-propylene diamine, ethanolamine or a mixture thereof, for example a mixture of ethylene diamine and ethanolamine.

In the process for preparing the silver catalyst of the present invention, the optionally used alkali metal promoter can be lithium compound, sodium compound, potassium compound, rubidium compound or cesium compound (such as nitrate, sulfate and hydroxide) or a mixture thereof, preferably the alkali metal promoter is one or more of lithium compound, potassium compound and cesium compound, such as cesium nitrate, lithium nitrate and/or potassium hydroxide, especially cesium nitrate. The alkali metal promoter is favorably added to the impregnation solution in such an amount that the alkali metal is present in the final catalyst in an amount of 0-2000 ppm by weight, preferably 5-2000 ppm by weight, more preferably 5-1500 ppm by weight, calculated on the alkali metal atom.

In the process for preparing the silver catalyst of the present invention, the optionally used alkaline-earth metal promoter can be one or more of magnesium compound, calcium compound, strontium compound and barium compound, such as oxide, oxalate, sulfate, acetate and nitrate of said elements, preferably barium compound and/or strontium compound, such as barium acetate and/or strontium acetate. The alkaline-earth metal promoter is favorably added to the impregnation solution in such an amount that the alkaline-earth metal is present in the final catalyst in an amount of 0-10000 ppm by weight, preferably 0-8000 ppm by weight, calculated on the alkaline-earth metal atom.

In the process for preparing the silver catalyst of the present invention, the optionally used rhenium promoter can be rhenium oxide, perrhenic acid, perrhenate, or a mixture thereof, preferably perrhenic acid and perrhenate, such as perrhenic acid, cesium perrhenate and ammonium perrhenate, particularly preferably ammonium perrhenate. The rhenium promoter is added to the impregnation solution in such an amount that the rhenium metal is present in the final catalyst in an amount of 0-2000 ppm, preferably 10-2000 ppm, more preferably 100-1000 ppm, calculated on the rhenium metal atom.

When the rhenium promoter is present in the impregnation solution, a co-promoter of the rhenium promoter can be added to further improve the activity, the selectivity and the stability of the obtained silver catalyst. The co-promoter of the rhenium promoter according to the present invention can be a compound of any transitional metal in the Periodic Table, or a mixture of transitional metal compounds, preferably an oxyacid of an element selected from Groups VIB and VIIB, and a salt thereof, for example, tungstenic acid, sodium tungstate, potassium tungstate, ammonium tungstate, cesium tungstate, molybdic acid, ammonium molybdate, ammonium metatungstate, and the like. The co-promoter of the rhenium promoter is used in such an amount that the co-promoter of the rhenium promoter is present in the final catalyst in an amount of 0-1000 ppm, preferably 0-500 ppm.

In one preferable embodiment of the process for preparing the silver catalyst of the present invention, firstly, a silver compound such as silver oxalate is dissolved into an aqueous solution of organic amine such as pyridine, butyl amine, ethylene diamine, 1,3-propylene diamine, ethanolamine or a mixture thereof, into which is added the optional alkali metal promoter, the optional alkaline-earth metal promoter, and the optional rhenium promoter and optionally its co-promoter to formulate an impregnation solution. Then the alumina support is impregnated with the obtained impregnation solution, filtered to dryness, and kept in air or a nitrogen-oxygen mixed gas with oxygen content of 21 vol % or less at 180-700° C., preferably 200-500° C. for 1-120 mins, preferably 2-60 mins to thermally decompose and activate.

A silver catalyst can be obtained by the process for preparing the catalyst of the present invention, and it can be used in a gas-solid phase catalytic oxidation of ethylene to produce ethylene oxide.

Therefore, according to yet another aspect of the present invention, the present invention provides a silver catalyst prepared according to the above process and useful in a gas-phase catalytic oxidation of ethylene to produce ethylene oxide, which catalyst contains the alpha-alumina support prepared according to the present invention and silver deposited thereon in an amount of 1-40 wt % calculated on silver atom based on the total weight of the silver catalyst, an optional alkali metal promoter, an optional alkaline-earth metal promoter and an optional rhenium promoter.

In one preferable embodiment of the silver catalyst of the present invention, the silver catalyst according to the present invention contains the alpha-alumina support prepared according to the present invention and silver deposited thereon in an amount of 1-40 wt % calculated on silver atom based on the total weight of the silver catalyst, an alkali metal promoter in an amount of 5-2000 ppm by weight calculated on the alkali metal atom, and a rhenium promoter in an amount of 10-2000 ppm by weight calculated on the rhenium atom.

Finally, the present invention also relates to a use of the silver catalyst according to the present invention in the production of ethylene oxide by the oxidation of ethylene.

Compared with the prior art, the present invention has the following advantage: the alumina support prepared according to the present invention can be used to produce a silver catalyst with a higher selectivity for the production of ethylene oxide by the catalytic oxidization of ethylene.

EXAMPLES

The present invention will be illustrated by the following examples, but the scope of the present invention is not limit thereto.

The Catalyst Performance Evaluation

The silver catalysts used in the examples of the present invention were tested in a laboratory micro-reactor evaluation apparatus for the catalytic reaction performance. In the micro-reactor evaluation apparatus, the reactor was a stainless steel reaction tube having an inner diameter of 4 mm. The reaction tube was disposed in a heating jacket. The loading volume of the catalyst was 1 mL. The inert filler was disposed in the lower portion so that the catalyst bed was located in the constant temperature area of the heating jacket.

The standard evaluation conditions for the catalytic activity and the selectivity used in the present invention were as follows:

The composition of the reaction gas (mol %):

| | |
|---|---|
| Ethylene ($C_2H_4$) | 28.0 ± 1.0 |
| Oxygen ($O_2$) | 7.4 ± 0.2 |
| Carbon dioxide ($CO_2$) | <3.0 |
| Ballast gas($N_2$) | Balance |
| Inhibitor 1,2-dichloroethane | 0.1 ppm-2.0 ppm |
| Reaction pressure | 2.1 MPa |
| Space velocity | 7000/h |
| The concentration of ethylene oxide (EO) in the effluent from the reactor | 2.5 mol % |
| Hour space yield | 344 g EO/ml Cat./h |

When the reaction becomes stable and reaches the above reaction conditions, the compositions of the gases at the inlet and the outlet of the reactor were continually measured. The measurement results, after applying the volume-shrinkage correction thereto, were used to calculate the selectivity according to the following formula:

$$S = \frac{\Delta EO}{\Delta EO + 0.5 \times \Delta CO_2} \times 100\%$$

wherein $\Delta EO$ was the ethylene oxide concentration difference between the outlet and the inlet of the reactor; and $\Delta CO2$ is the carbon dioxide concentration difference between the outlet and the inlet of the reactor. Ten or more sets of experiment data were taken and averaged as the experiment result of that day.

The Preparation for Support

Example 1

Comparative

The first part of starting materials of 3725 g trihydrate alpha-alumina, 1095 g pseudo-boehmite and 10 g $BaSO_4$ was put into a mixer to mix homogenously. The second part of starting materials having the same compositions as the above was mixed homogenously. Two parts of starting materials were put into a kneader. 160 g NH$_4$F was completely dissolved into 1.90 L of a diluted aqueous nitric acid solution (nitric acid:water=1:3 v/v), added to the kneader to knead into an extrudable paste. Finally, the paste was put into an extruder to extrude into column-like bodies with an outer diameter of 8.0 mm and a length of 6.0 mm, and dried at a temperature of 80-120° C. for 2 hours or more until the free-water content of the bodies decreased to the level below 10 wt %.

The dried column-like bodies were put into a natural gas kiln, heated up over a period of 18 hours from room temperature to 1250° C., and kept at that temperature constantly for 4 hours to obtain an alpha-alumina sample numbered as Support 1. The relevant physical properties of Support 1 are listed in Table 1.

Example 2

Inventive

The first part of starting materials of 3725 g trihydrate alpha-alumina, 1095 g pseudo-boehmite and 10 g BaSO$_4$ was put into a mixer to mix homogenously. The second part of starting materials having the same compositions as the above was mixed homogenously. Two parts of starting materials were put into a kneader. 160 g NH$_4$F and 80 g potassium nitrate were completely dissolved into 1.80 L of a diluted aqueous nitric acid solution (nitric acid:water=1:3 v/v), added to the kneader to knead into an extrudable paste. Finally, the paste was put into an extruder to extrude into column-like bodies with an outer diameter of 8.0 mm and a length of 6.0 mm, and dried at a temperature of 80-120° C. for 2 hours or more until the free-water content of the bodies decreased to the level below 10 wt %.

The dried column-like bodies were put into a natural gas kiln, heated up over a period of 18 hours from room temperature to 1250° C., and kept at that temperature constantly for 4 hours to obtain an alpha-alumina sample numbered as Support 2. The relevant physical properties of Support 2 are listed in Table 1.

Example 3

Inventive 200 g Support 2 was put into a glass vessel, into which was added 400 g deionized water, sonically oscillated for 20 mins, thereafter stood for 10 mins, then filtered to remove the aqueous solution, heated in an air stream of 380° C. for 3 mins, and cooled to produce Support 3. The relevant physical properties of Support 3 are listed in Table 1.

TABLE 1

The physical properties of Supports 1-3

| Support No. | Strength (N/particle) | Water Absorption (%) | Specific Surface Area (m$^2$/g) | Pore Volume (ml/g) | K (ppm) |
|---|---|---|---|---|---|
| 1 | 79 | 55.8 | 1.131 | 0.5027 | 60 |
| 2 | 141 | 58.08 | 0.831 | 0.5755 | 230 |
| 3 | 130 | 57.59 | 1.05 | 0.5869 | 110 |

The Preparation for Catalysts 1-3

To a glass flask with a stirrer were added 48.2 g ethylene diamine, 16.3 g ethanolamine and 105.8 g deionized water to give a mixed solution. 108.1 g of silver oxalate was slowly added to the mixed solution while stirring. The solution temperature was maintained at a temperature of below 40° C., and silver oxalate was dissolved completely. Then 6.01 ml of an aqueous cesium nitrate solution having a concentration of 0.03995 g/ml calculated as the cesium atom weight, 9.26 ml of an aqueous ammonium perrhenate solution having a concentration of 0.0162 g/ml calculated as the rhenium atom weight, and 6.40 ml of an aqueous sodium tungstate solution having a concentration of 0.00938 g/ml calculated as the tungsten atom weight were successively added. The solution was mixed homogenously to give an impregnation solution for use.

Each 20 g of the above prepared Supports 1-3 were placed into glass vessels which can be vacuumed, into which were poured the above formulated impregnation solutions until the supports were immerged, vacuumed to a pressure below 10 mmHg, maintained for 10 mins, filtered to remove the redundant solution, then heated in an air stream at 260° C. for 3 mins, and cooled to give Silver Catalysts 1-3.

TABLE 2

The composition of the silver catalysts (by weight)

| Silver Catalyst | Cs (PPM) | Re (PPM) | Ag % | Na (PPM) |
|---|---|---|---|---|
| 1 | 765 | 304 | 20.92 | 213 |
| 2 | 733 | 314 | 20.94 | 164 |
| 3 | 757 | 291 | 20.28 | 129 |

Under the evaluation conditions given in the above section "The catalyst performance evaluation", the Silver Catalysts 1-3 were evaluated for the activity and selectivity of the catalysts in the micro-reactor evaluation apparatus. The results are shown in Table 3.

TABLE 3

Evaluation data for Catalysts 1-3

| | | micro-reactor evaluation data (the 20$^{th}$ day) Space Velocity: 7000 hr$^{-1}$; EO concentration: 2.50 mol % | |
|---|---|---|---|
| Silver Catalyst | Support No. | Reaction Temperature (° C.) | Selectivity (%) |
| 1 | 1 | 233.6 | 83.59 |
| 2 | 2 | 240.6 | 85.73 |
| 3 | 3 | 237.6 | 85.58 |

It is clear from Table 3 that in comparison with Comparative Silver Catalyst I, the Silver Catalyst 2 made from the support prepared by potassium melt technology has a higher selectivity. Furthermore, the Silver Catalyst 3, made from the Support 3 that was subjected to a subsequent water-washing procedure, has a better catalytic activity than the Silver Catalyst 2.

The invention claimed is:

1. An alpha-alumina support for a silver catalyst, comprises:
   alpha-alumina; and
   a potassium compound obtained from calcining potassium nitrate at a temperature of 900-1600° C.,
   wherein the alpha-alumina support has a specific surface area of 0.2-2.0 m$^2$/g, a pore volume of 0.30-0.85 ml/g, and a potassium content of 0.001-2.0%, calculated based on the weight of potassium element over the weight of the support, wherein the alpha-alumina support is capable of absorbing an amount of water that is not lower than 30% of the weight of the support, and wherein the alpha-alumina support is free of silver.

2. The alpha-alumina support of claim 1, wherein the potassium content is 0.011-2.0%, calculated based on the weight of potassium element over the weight of the support.

3. The alpha-alumina support of claim 1, further comprising a barium compound obtained from calcining barium nitrate at a temperature of 900-1600° C., wherein the alpha-alumina support has a barium content less than 2.0%, calculated based on the weight of barium element over the weight of the support.

4. A silver catalyst, comprising: an alpha-alumina support of claim 1, silver deposited on the alpha-alumina support, an optional alkali metal promoter, an optional alkaline-earth metal promoter, a rhenium promoter and optionally a co-promoter of rhenium promoter, wherein silver is present in the silver catalyst in an amount of 1-40%, calculated based on silver atom and the total weight of the silver catalyst, wherein the optional alkali metal promoter is present in the silver catalyst in an amount of 0-2000 ppm, calculated based on alkali metal atom and the total weight of the silver catalyst, wherein the rhenium promoter is present in the silver catalyst in an amount of less than 2000 ppm, calculated based on rhenium atom and the total weight of the silver catalyst, wherein the optional alkaline-earth metal promoter is present in the silver catalyst in an amount of 0-10000 ppm, calculated based on alkaline-earth metal atom and the total weight of the silver catalyst.

* * * * *